(12) United States Patent
Kim et al.

(10) Patent No.: US 6,316,245 B1
(45) Date of Patent: Nov. 13, 2001

(54) MUTANT CELLS OF PICHIA

(75) Inventors: Sang Yong Kim, Kyonggi; Deok Kun Oh, Chonbuk; Soo Ryun Jung, Seoul, all of (KR)

(73) Assignee: BioNgene Co., Ltd., Seoul (KR)

( * ) Notice: Subject to any disclaimer, the term of this patent is extended or adjusted under 35 U.S.C. 154(b) by 0 days.

(21) Appl. No.: 09/383,384

(22) Filed: Aug. 26, 1999

Related U.S. Application Data

(62) Division of application No. 09/154,218, filed on Sep. 16, 1998, now Pat. No. 6,001,616.

(51) Int. Cl.$^7$ ................................. C12N 1/16; C12P 7/02
(52) U.S. Cl. .................. 435/255.5; 435/158; 435/938
(58) Field of Search ................................. 435/255.5, 938, 435/158

(56) References Cited

U.S. PATENT DOCUMENTS 4,879,231 * 11/1989 Stroman et al. ................. 435/254.23

OTHER PUBLICATIONS

Hajny, et al., *Applied Microbiology*, 12:3, pp. 240–246, May 1964.

Ishizuka, et al., *Journal of Fermentation and Bioengineering*, 68:5, pp. 310–314, 1989.

Aoki, et al., *Biotechnology Letters*, 15:4, pp. 383–388, Apr. 1993.

Hajny, et al.: Erythritol Production by a Yeastlike Fungus, Applied Microbiology, 12:3, pp. 240–246, May 1964.

Ishizuka, et al.: Breeding of a Mutant of Aureobasidium sp. With High Erythritol Production, Journal of Fermentation and Bioengineering, 68:5, pp. 310–314, 1989.

Aoki, et al.: Microbial Transformation of Sucrose and Glucose to Erythritol, Biotechnology Letters, 15:4, pp. 383–388, Apr. 1993.

* cited by examiner

*Primary Examiner*—Herbert J. Lilling
(74) *Attorney, Agent, or Firm*—Kenyon & Kenyon

(57) ABSTRACT

The present invention relates to a fermentation process to have a high productivity with a novel mutant of Pichia sp., more specifically, for preparing erythritol under optimal fermentation conditions for maximum erythritol production by optimizing the environmental conditions of culture such as pH, temperature and by controlling osmotic pressure. A two-stage fermentation was performed to control osmotic pressure. Osmotic pressure was adjusted to a low level during growth phase and to a relatively high level during production phase by adding continuously glucose and NaCl or KCl. Therefore, erythritol production could be increased.

1 Claim, No Drawings

MUTANT CELLS OF PICHIA

CROSS REFERENCE TO RELATED APPLICATIONS

The present application is a division of application Ser. No. 09/154,218 filed Sep. 16, 1998 now U.S. Pat. No. 6,001,616, the subject matter of which is incorporated herein by reference.

BACKGROUND OF THE INVENTION

1. Field of the Invention

The present invention relates to a fermentation process to have a high productivity with a novel mutant of Pichia, more specifically, for preparing erythritol under optimal fermentation conditions for maximum erythritol production by optimizing the environmental conditions of culture such as pH, temperature and by controlling osmotic pressure using a two stage fermentation, in which osmotic pressure is adjusted to a low level during growth phase and to a relatively high level during production phase by adding continuously glucose and NaCl or KCl.

2. Description of Prior Art

Erythritol, a four carbon sugar alcohol, is a naturally occurring substance and is widely distributed in nature. Like most of the other polyols, it is a metabolite or storage compound for seaweeds and mushrooms. Fruits like melons, grapes and pears also contain erythritol. As it is often produced by bacteria, fungi, and yeasts, erythritol also occurs frequently in fermented food systems like wines or beers, and processed vegetables such as soy sauce or the oriental miso bean paste.

Erythritol is a moderately sweet bulking agent with 60 to 70 percent of the sweetness of sucrose in a ten percent solution. Its high negative heat of solution provides the crystalline material with a strong cooling effect. As it has a taste which is very close to sucrose and with no bitter aftertaste, it is ideal to improve the taste of a combination with intense sweeteners like aspartame.

Being a small molecule, erythritol has strong colligative properties, i.e. a strong freezing point depression and boiling point elevation effect as well as a high osmotic pressure. In combination with its low hygroscopicity and viscosity in solution, it is very useful to reduce and control the water activity of foodstuffs.

Erythritol production from its natural sources such as fruits and vegetables is impractical due to the relative small amounts. Erythritol can be chemically produced by reduction of meso-tartarate, oxidation and reduction of 4,6-o-ethylidene-D-glucose, hydrolysis of dealdehyde starch, or addition of hydrogen. Since erythritol production by the chemical methods has been found to be expensive, it is worthwhile to explore an alternative method for the effective production of erythritol using microorganisms.

Erythritol can be produced by microbial methods with the osmophilic yeasts, especially species of the genus Torulopsis, such as *T. magnoliae, T. veratilis,* and *T. candida; Endomzycopsis chodati; Hansenula supelliculsa; Pichia miso; Monilliella tomentosa* var. *pollinis; Trigonopsis variabilis;* Trichosporonoides; *Candida zeylanoides;* and Aureobasidium. Some bacteria such as *Leuconostoc oenos* can also produce erythritol. *Monilliella tomentosa* var. *pollinis* produced erythritol on a medium containing 35.7% glucose with 45.6% yield. Erythritol production using this strain did not apply to industrial scale due to by-products such as glycerol and ribitol. Industrial production of erythritol has been performed by a mutant of Aureobasidium. The mutant was isolated and developed by cooperative study of Nikken Chemical and National Research Institute of Japan. The mutant produced erythritol with 47.6% yield on a medium containing 22.5% glucose and 2 g/L.h volumetric productivity.

It was found that the most polyols producing strains can grow on the conditions of high osmotic pressure such as the high concentration of sugars and salts. This fact suggests that polyols production has the relation to osmotic pressure. Reed et al. reported that glycerol productivity was improved by culturing a glycerol producing strain under the conditions of high osmotic pressure. However, erythritol production by controlling osmotic pressure has not been reported.

Therefore, in this invention, a wild strain of Pichia sp., an isolated strain from the air in 40% sucrose solution at Woosuk University, Chonbuk, Korea was selected to produce erythritol. The wild strain was mutated with NTG (N-methyl-N'-nitro-N-nitroguanidine) treatment. One of mutants has superior properties to the wild strain in erythritol yield from glucose, volumetric productivity, and sugar tolerance. By using the mutant of Pichia sp., the effect of osmotic pressure on erythritol production was investigated and two-stage fermentation, in which osmotic pressure was adjusted to a low level during growth phase and to a relatively high level during production phase, was performed by adding continuously glucose and NaCl or KCl.

SUMMARY OF THE INVENTION

The object of the present invention is to provide novel mutants cells of Pichia sp., which were deposited to Korean Culture Center of Microorganism Department of Feed Engineering, College of Engineering, Yonsei University, Sodaemun-gu, Seoul 120–749, Korea, with accession number KCCM-10129 on Jun. 12, 1998 under Budapest treaty, for preparing erythritol with high productivity.

The other object of the present invention is to provide the optimal fermentation conditions for maximum production of erythritol using mutant cells by controlling following conditions;

i) fermenting glucose medium with mutant cells wherein
  a) composition of medium for maximum production of erythritol consists of 10~50 (w/v)% of glucose, 0.5~4.0 (w/v)% of yeast extract, 0.2~1.0 (w/v)% of $KH_2PO_4$, 0.01~0.04 (w/v)% of $MgSO_4.7H_2O$, 0~5 (w/v)% of NaCl, 0~5 (w/v)% of KCl.
  b) pH of culture medium is 4.5~5.5.
  c) temperature of cultivation is 27~33° C.
  d) aeration rate of the medium is 0.5~2.0 volume of air per volume of medium per minute; and
  e) agitation speed of the medium is 300~1200 rpm;
ii) removing the mutant cells and other residue from the fermentation medium; and
iii) separating and recovering erythritol from the fermentation medium of step (ii).

The further object of the present invention is to provide a fermentation process, wherein the mutant cells used for fermentation are prepared by cultivating Pichia sp. KCCM-10129 in YM medium containing 0.8~1.2 (w/v)% of glucose, 0.4~0.6 (w/v)% of peptone, 0.2~0.4 (w/v)% of yeast extract, and 0.2~0.4 (w/v)% of malt extract at 27~33° C. for 20~28 h.

The further object of the present invention is to provide a fermentation process, wherein the osmotic pressure is controlled by i) the osmotic pressure is adjusted to 0.2~0.7 Osm/kg during growth phase and 0.8~1.2 Osm/kg during erythritol production phase; and ii) feeding solution containing glucose, NaCl or KCl are continuously or intermittently fed into the culture broth during erythritol production phase to be 10~20% of glucose, 0~5% of NaCl or 0~5% of KCl respectively, for the effective production of erythritol.

The further object of the present invention is to provide a method of isolating Pichia sp. mutants comprising the steps of:

i) spreading and culturing a wild type Pichia sp. on yeast-malt (YM) medium containing 0.01% NTG (N-methyl-N'-nitro-N-nitroguanidine);

ii) isolating the produced colonies at least three times on YM medium;

iii) spreading and culturing the colonies of step (ii) on YM medium under UV illumination of 250~270 nm; and iv) isolating the growing colonies.

DETAILED DESCRIPTION OF THE INVENTION

The present invention concerns a method of obtaining erythritol with a high yield and a high volumetric productivity in Pichia sp. mutant by controlling osmotic pressure.

The mutant cells used for the present invention are isolated by following method.

Pichia sp. was incubated at 28~32° C. for 24 h on the fermentation agar plate containing 18~22% glucose. A single colony was incubated in a 250-mL flask containing 50 mL of YM broth. It was incubated at 28~32° C. and 220~260 rpm until the optical density of culture broth at 600 nm reached at 1.0. The grown cells were collected by centrifugation at 3000 g for 20 mn and washed with 0.1 M citrate buffer pH 5.5. The collected cells were resuspended in the buffer solution containing 0.01% NTG and incubated at 28~32° C. for 25~35 min. After NTG treatment, the cells were incubated at 28~32° C. for 8~12 h in YM broth and plated on the agar plate containing 40% glucose and 2.0% yeast extract for the selection of a high erythritol producing mutant. Single colonies were selected as fast growing mutants. The selected colonies were transferred on the fermentation medium containing 18~22% glucose to test erythritol producing activity in shake flask. After incubating at 28~32° C. and 220~260 rpm in 100~140 h, a high erythritol producing mutant was selected and colony produced is separated by repeating separation method more than 3 times. The obtained colony is again spread and cultured to YM medium under UV illumination of 250~270 nm. Finally, growing colony is isolated and obtained as mutant cells and used as a producing strain in this invention. These mutant cells were deposited to Korean Culture Center of Microorganism with accession number KCCM-10129 under Budapest Treaty.

The following is fermentation method for producing erythritol using mutants cells.

Seed Culture

A frozen (-70° C.) mutant cells of Pichia sp. are cultivated in a 250-mL flask containing 40~60 mL growth medium (0.8~1.2% glucose, 0.4~0.6% peptone, 0.3~0.5% yeast extract and 0.2~0.4% malt extract) at 28~32° C. and 220~260 rpm for 20~28 h and this seed culture was transferred to a 5-L fermentor for producing erythritol in main culture.

Main Culture

Flask experiments with fermentation medium were performed at 28~32° C. and 220~260 rpm in 80~120 h. The fermentation medium consisted of 10~50% glucose as carbon source and 0.5~4.0% yeast extract as nitrogen source; and 0.2~1.0% $KH_2PO_4$ and 0.01~0.04% $MgSO_4.7H_2O$ were used to be inorganic sources. For the experimental purpose, glucose concentration was adjusted. Batch and fed-batch culture in the fermentor were performed at 27~33° C. and pH 5.5 during the fermentation. Aeration rate was in the range of 0.5~2.0 vvm. Agitation speed was gradually increased from 300 to 1,200 rpm to maintain the level of dissolved oxygen above 20%. Working volume in batch culture was 3 L. Fed-batch culture was performed with initial medium of 1.8 L and finial volume was 3 L by adding continuously 1.2 L of feeding medium. The initial medium of 1.8 L, consisted of 144~288 g glucose and 60 g yeast extract, 15 g $KH_2PO_4$ and 0.6 g $MgSO_4.7H_2O$. The feeding medium of 1.2 L contained 912~1056 g glucose and 60 g NaCl. The concentration of glucose during fermentation could be controlled in the range of 7.0~9.0%, 9. 0~11.0%, 11.0%, 13.0~15.0%, and 15.0~17.0% for the respective its concentration settings of 8.0%, 10.0%, 12.0%, 14.0%, 16.0% by adjusting pump speed of the feeding medium.

The fermentation process is preferably carried out by fed-batch process. After glucose was completely consumed in the medium, the amount of erythritol is measured by high performance liquid chromatography equipped with Carbohydrate Analysis column. Dry cell weight is estimated by using a calibration curve made from relationship between optical density at 600 nm and dry cell weight. Glucose is measured by glucose oxidase kit (Sigma, USA). Osmotic pressure is determined by automatic semi-micro osmometer. The specific growth rate is determined by the slope from the plotting for time(X) and logarithmic cell mass(Y), and the specific production rate of erythritol is determined by dividing cell mass over the slope of erythritol production against time using polynomial regression.

The measured yield of erythritol is 45~55% of glucose consumption and volumetric productivity is 2.0~3.0 g/L.h, which are increased by 2~5 fold compared with conventional fermentation yield and productivity.

Finally, the fermentation medium is centrifuged for removing cells and other residue, and the supernatant is filtered and dialyzed for obtaining erythritol.

The present invention can be explained more specifically by following examples.

EXAMPLE I

The frozen (-70° C.) mutant cells of Pichia sp. (KCCM-10129) are cultivated in a 250-ml flask containing 50 ml growth medium(0.8~1.2% glucose, 0.4~0.6% peptone, 0.3~0.5% yeast extract and 0.2~0.4% malt extract) at 28~32° C. and 220~260 rpm. The seed cells are cultivated in a 5 L fermentor containing fermentation medium, which consisted of 10~40% glucose and 2.0% yeast extract, 0.5% $KH_2PO_4$, 0.02% $MgSO_4 .7H_2O$ for producing erythritol in main culture. Fermentor experiments with fermentation medium were performed at 30° C. and pH 5.5 during the fermentation. Aeration rate was in the range of 0.5~2.0 vvm. Agitation speed was gradually increased from 300 to 1,200 rpm to maintain the level of dissolved oxygen above 20%. Working volume was 3 L.

After 40 hours fermentation, the amount of erythritol from 10% glucose (Osmolarity=0.52 Osm/kg) is measured by HPLC equipped with Carbohydrate Analysis column. The obtained erythritol is 30 g/L and volumetric productivity is 0.75 g/L.h.

After 66 hours fermentation, the amount of erythritol from 20% glucose (Osmolarity=0.99 Osm/kg) is measured by HPLC equipped with Carbohydrate Analysis column. The obtained erythritol is 89 g/L and volumetric productivity is 1.35 g/L.h.

After 90 hours fermentation, the amount of erythritol from 30% glucose (Osmolarity=1.56 Osm/kg) is measured by HPLC equipped with Carbohydrate Analysis column. The obtained erythritol is 158 g/L volumetric productivity is 1.76 g/L.h.

After 160 hours fermentation, the amount of erythritol from 40% glucose (Osmolarity=2.08 Osm/kg) is measured by HPLC equipped with Carbohydrate Analysis column. The obtained erythritol is 85 g/L volumetric productivity is 0.53 g/L.h, and residual glucose is 8.9%.

EXAMPLE II

The frozen (−70° C.) mutant cells of Pichia sp. (KCCM-10129) are cultivated in a 250-ml flask containing 50 ml growth medium(0.8~1.2% glucose, 0.4~0.6% peptone, 0.3~0.5% yeast extract and 0.2~0.4% malt extract) at 28~32° C. and 220~260 rpm. The seed cells are cultivated in a 5 L fermentor containing fermentation medium, which consisted of 15% glucose and 0.75% yeast extract, 0.5% $KH_2PO_4$, 0.02% $MgSO_4.7H_2O$ 0.0~0.84M KCl for producing erythritol in main culture. Fermentor experiments with fermentation medium were performed at 30° C. and pH 5.5 during the fermentation. Aeration rate was in the range of 0.5~2.0 vvm in 60 h. Agitation speed was gradually increased from 300 to 1,200 rpm to maintain the level of dissolved oxygen above 20%. Working volume was 3 L.

After 60 hours fermentation, the amount of erythritol from 15% glucose and 0.0M KCl (Osmolarity=0.79 Osm/kg) is measured by HPLC equipped with Carbohydrate Analysis column. The obtained erythritol is 58 g/L and volumetric productivity is 0.97 g/L.h.

After 60 hours fermentation, the amount of erythritol from 15% glucose and 0.27M KCl (Osmolarity=1.07 Osm/kg) is measured by HPLC equipped with Carbohydrate Analysis column. The obtained erythritol is 68 g/L and volumetric productivity is 1.13 g/L.h.

After 60 hours fermentation, the amount of erythritol from 15% glucose and 0.62M KCl (Osmolarity=1.66 Osm/kg) is measured by HPLC equipped with Carbohydrate Analysis column. The obtained erythritol is 81 g/L and volumetric productivity is 1.35 g/L.h.

After 60 hours fermentation, the amount of erythritol from 15% glucose and 0.0M KCl (Osmolarity=2.08 Osm/kg) is measured by HPLC equipped with Carbohydrate Analysis column. The obtained erythritol is 39 g/L and volumetric productivity is 0.65 g/L.h, and residual glucose is 1.5%.

EXAMPLE III

The frozen (−70° C.) mutant cells of Pichia sp. (KCCM-10129) are cultivated in a 250ml flask containing 50 ml growth medium(0.8~1.2% glucose, 0.4~0.6% peptone, 0.3~0.5% yeast extract and 0.2~0.4% malt extract) at 28~32° C. and 220~260 rpm. The seed cells are cultivated in a 5 L fermentor containing fermentation medium, which consisted of 15% glucose and 0.75% yeast extract, 0.5% $KH_2PO_4$, 0.02% $MgSO_4.7H_2O$ 0.0~0.82M NaCl for producing erythritol in main culture. Fermentor experiments with fermentation medium were performed at 30° C. and pH 5.5 during the fermentation. Aeration rate was in the range of 0.5~2.0 vvm in 60 h. Agitation speed was gradually increased from 300 to 1,200 rpm to maintain the level of dissolved oxygen above 20%. Working volume was 3 L.

After 60 hours fermentation, the amount of erythritol from 15% glucose and 0.0M NaCl (Osmolarity=0.79 Osm/kg) is measured by HPLC equipped with Carbohydrate Analysis column. The obtained erythritol is 58 g/L and volumetric productivity is 0.97 g/L.h.

After 60 hours fermentation, the amount of erythritol from 15% glucose and 0.27M NaCl (Osmolarity=1.07 Osm/kg) is measured by HPLC equipped with Carbohydrate Analysis column. The obtained erythritol is 67 g/L and volumetric productivity is 1.12 g/L.h.

After 60 hours fermentation, the amount of erythritol from 15% glucose and 0.61M NaCl (Osmolarity=1.64 Osm/kg) is measured by HPLC equipped with Carbohydrate Analysis column. The obtained erythritol is 79 g/L and volumetric productivity is 1.32 g/L h, and residual glucose is 0.3%.

After 60 hours fermentation, the amount of erythritol from 15% glucose and 0.0M KCl (Osmolarity=2.06 Osm/kg) is measured by HPLC equipped with Carbohydrate Analysis column. The obtained erythritol is 36 g/L and volumetric productivity is 0.60 g/L.h, and residual glucose is 1.9%.

EXAMPLE IV

The frozen (−70° C.) mutant cells of Pichia sp. (KCCM-10129) are cultivated in a 250-ml flask containing 50 ml growth medium(0.8~1.2% glucose, 0.4~0.6% peptone, 0.3~0.5% yeast extract and 0.2~0.4% malt extract) at 28~32° C. and 220~260 rpm. The seed cells are cultivated in a 5 L fermentor containing 3 L fermentation medium, which consisted of 15% glucose, 0.75% yeast extract, 0.5% $KH_2PO_4$, and 0.02% $MgSO_4.7H_2O$ for producing erythritol in main culture. Fermentation is performed at 30° C. for 60 hours and aeration rate is 1.0~2.0 vvm, agitation speed is 300~1200 rpm, and pH is 3.5~8.5.

After 60 hours fermentation, the amount of erythritol from 15% glucose and pH 3.5 is measured by HPLC equipped with Carbohydrate Analysis column. The obtained erythritol is 40 g/L, volumetric productivity is 0.67 g/L.h, and residual glucose is 1.7%.

After 60 hours fermentation, the amount of erythritol from 15% glucose and pH 5.5 is measured by HPLC equipped with Carbohydrate Analysis column. The obtained erythritol is 58 g/L and volumetric productivity is 0.97 g/L.h.

After 60 hours fermentation, the amount of erythritol from 15% glucose and pH 7.5 is measured by HPLC equipped with Carbohydrate Analysis column. The obtained erythritol is 40 g/L, volumetric productivity is 0.67 g/L.h, and residual glucose is 0.8%.

EXAMPLE V

The frozen (−70° C.) mutant cells of Pichia sp. (KCCM-10129) are cultivated in a 250-ml flask containing 50 ml growth medium(0.8~1.2% glucose, 0.4~0.6% peptone, 0.3~0.5% yeast extract and 0.2~0.4% malt extract) at 28~32° C. and 220~260 rpm. The seed cells are cultivated in a 5 L fermentor containing 3 L fermentation medium, which consisted of 15% glucose, 0.75% yeast extract, 0.5% $KH_2PO_4$, and 0.02% $MgSO_4.7H_2O$ for producing erythritol in main culture. Fermentation is performed at pH 5.5 for 60 hours and aeration rate is 1.0~2.0 vvm, agitation speed is 300~1200 rpm, and temperature is 26~34° C.

After 60 hours fermentation, the amount of erythritol from 15% glucose and 26° C. is measured by HPLC equipped with Carbohydrate Analysis column. The obtained erythritol is 32 g/L, volumetric productivity is 0.53 g/L.h, and residual glucose is 2.4%.

After 60 hours fermentation, the amount of erythritol from 15% glucose and 30° C. is measured by HPLC equipped with Carbohydrate Analysis column. The obtained erythritol is 58 g/L and volumetric productivity is 0.97 g/L.h.

After 60 hours fermentation, the amount of erythritol from 15% glucose and 34° C. is measured by HPLC equipped with Carbohydrate Analysis column. The obtained erythritol is 45 g/L and volumetric productivity is 0.75 g/L.h, and residual glucose is 1.0%.

EXAMPLE VI

The frozen (−70° C.) mutant cells of Pichia sp. (KCCM-10129) are cultivated in a 250-ml flask containing 50 ml growth medium(0.8~1.2% glucose, 0.4~0.6% peptone, 0.3~0.5% yeast extract and 0.2~0.4% malt extract) at 28~32° C. and 220~260 rpm. The seed cells are cultivated in a 5 L fermentor containing fermentation medium, which consisted of 10~40% glucose and 2.0% yeast extract, 0.5% $KH_2PO_4$, 0.02% $MgSO_4.7H_2O$ for producing erythritol in main culture. Fermentor experiments with fermentation medium were performed at 30° C. and pH 5.5 during the fermentation. Aeration rate was in the range of 0.5~2.0 vvm. Agitation speed was gradually increased from 300 to 1,200 rpm to maintain the level of dissolved oxygen above 20%. Working volume was 3 L.

Fermentation with 10% glucose (Osmolarity=0.52 Osm/kg) is performed. The obtained specific growth rate is 0.13 $h^{-1}$ and specific production rate of erythritol is 0.05 g/g.h.

Fermentation with 20% glucose (Osmolarity=0.99 Osm/kg) is performed.

The obtained specific growth rate is 0.13 $h^{-1}$ and specific production rate of erythritol is 0.10 g/g.h.

Fermentation with 30% glucose (Osmolarity=1.56 Osm/kg) is performed. The obtained specific growth rate is 0.13 $h^{-1}$ and specific production rate of erythritol is 0.13 g/g.h.

Fermentation with 40% glucose (Osmolarity=2.08 Osm/kg) is performed. The obtained specific growth rate is 0.13 $h^{-1}$ and specific production rate of erythritol is 0.09 g/g.h.

EXAMPLE VII

The frozen (−70° C.) mutant cells of Picha sp. (KCCM-10129) are cultivated in a 250-ml flask containing 50 ml growth medium(0.8~1.2% glucose, 0.4~0.6% peptone, 0.3~0.5% yeast extract and 0.2~0.4% malt extract) at 28~32° C. and 220~260 rpm. The seed cells are cultivated in a 5 L fermentor containing fermentation medium, which consisted of 15% glucose and 0.75% yeast extract, 0.5% $KH_2PO_4$, 0.02% $MgSO_4.7H_2O$ 0.0~0.84M KCl for producing erythritol in main culture. Fermentor experiments with fermentation medium were performed at 30° C. and pH 5.5 during the fermentation. Aeration rate was in the range of 0.5~2.0 vvm in 60 h. Agitation speed was gradually increased from 300 to 1,200 rpm to maintain the level of dissolved oxygen above 20%. Working volume was 3 L.

Fermentation with 15% glucose and 0.0M KCl (Osmolarity=0.79 Osm/kg) is performed. The obtained specific growth rate is 0.12 $h^{-1}$ and specific production rate of erythritol is 0.07 g/g.h.

Fermentation with 15% glucose and 0.27M KCl (Osmolarity=1.07 Osm/kg) is performed. The obtained specific growth rate is 0.11 $h^{-1}$ and specific production rate of erythritol is 0.10 g/g.h.

Fermentation with 15% glucose and 0.62M KCl (Osmolarity=1.66 Osm/kg) is performed. The obtained specific growth rate is 0.10 $h^{-1}$ and specific production rate of erythritol is 0.13 g/g.h.

Fermentation with 15% glucose and 0.84M KCl (Osmolarity=2.08 Osm/kg) is performed. The obtained specific growth rate is 0.06 $h^{-1}$ and specific production rate of erythritol is 0.09 g/g.h.

EXAMPLE VIII

The frozen (−70° C.) mutant cells of Pichia sp. (KCCM-10129) are cultivated in a 250-ml flask containing 50 ml growth medium(0.8~1.2% glucose, 0.4~0.6% peptone, 0.3~0.5% yeast extract and 0.2~0.4% malt extract) at 28~32° C. and 220~260 rpm. The seed cells are cultivated in a 5 L fermentor containing fermentation medium, which consisted of 15% glucose and 0.75% yeast extract, 0.5% $KH_2PO_4$, 0.02% $MgSO_4.7H_2O$ 0.0~0.82M NaCl for producing erythritol in main culture. Fermentor experiments with fermentation medium were performed at 30° C. and pH 5.5 during the fermentation. Aeration rate was in the range of 0.5~2.0 vvm in 60 h. Agitation speed was gradually increased from 300 to 1,200 rpm to maintain the level of dissolved oxygen above 20%. Working volume was 3 L.

Fermentation with 15% glucose and 0.0M NaCl (Osmolarity=0.79 Osm/kg) is performed. The obtained specific growth rate is 0.12 $h^{-1}$ and specific production rate of erythritol is 0.07 g/g.h.

Fermentation with 15% glucose and 0.27M NaCl (Osmolarity=1.07 Osm/kg) is performed. The obtained specific growth rate is 0.11 $h^{-1}$ and specific production rate of erythritol is 0.10 g/g.h.

Fermentation with 15% glucose and 0.61M NaCl (Osmolarity=1.64 Osm/kg) is performed. The obtained specific growth rate is 0.10 $h^{-1}$ and specific production rate of erythritol is 0.12 g/g.h.

Fermentation with 15% glucose and 0.82M NaCl (Osmolarity=2.06 Osm/ kg) is performed. The obtained specific growth rate is 0.06 $h^{-1}$ and specific production rate of erythritol is 0.08 g/g.h.

EXAMPLE IX

The frozen (−70° C.) mutant cells of Pichia sp. (KCCM-10129) are cultivated in a 250-ml flask containing 50 ml growth medium(0.8~1.2% glucose, 0.4~0.6% peptone, 0.3~0.5% yeast extract and 0.2~0.4% malt extract) at 28~32° C. and 220~260 rpm. The seed cells are cultivated in a 5 L fermentor for producing erythritol in main culture. Fermentor experiments with fermentation medium were performed at 30° C. and pH 5.5 during the fermentation. Aeration rate was in the range of 0.5~2.0 vvm. Agitation speed was gradually increased from 300 to 1,200 rpm to maintain the level of dissolved oxygen above 20%. Fed-batch culture was performed with initial medium of 1.8 L and finial volume was 3 L by adding continuously 1.2 L of feeding medium. The initial medium of 1.8 L, consisted of 144~288 g glucose and 60 g yeast extract, 15 g $KH_2PO_4$ and 0.6 g $MgSO_4.7H_2O$. The feeding medium of 1.2 L contained 912~1056 g glucose. The concentration of glucose during fermentation could be controlled in the range of 7.0~9.0%, 9.0~11.0%, 11.0%, 13.0~15.0%, and 15.0~17.0% for the respective its concentration settings of 8.0%, 10.0%, 12.0%, 14.0%, 16.0% by adjusting pump speed of the feeding medium.

After 104 hours fermentation, the amount of erythritol from 40% glucose is measured by controlling the glucose concentration to 8.0%. The obtained erythritol is 167 g/L, volumetric productivity is 1.61 g/L.h.

After 86 hours fermentation, the amount of erythritol from 40% glucose is measured by controlling the glucose concentration to 12.0%. The obtained erythritol is 205 g/L, volumetric productivity is 2.38 g/L.h.

EXAMPLE X

The frozen (−70° C.) mutant cells of Pichia sp. (KCCM-10129) are cultivated in a 250-ml flask containing 50 ml growth medium(0.8~1.2% glucose, 0.4~0.6% peptone, 0.3~0.5% yeast extract and 0.2~0.4% malt extract) at 28~32° C. and 220~260 rpm. The seed cells are cultivated in a 5 L fermentor containing fermentation medium, which consisted of 15% glucose and 0.75% yeast extract, 0.5% $KH_2PO_4$, 0.02% $MgSO_4.7H_2O$ for producing erythritol in main culture. Fermentor experiments with fermentation medium were performed at 30° C. and pH 5.5 during the fermentation. Aeration rate was in the range of 0.5~2.0 vvm. Agitation speed was gradually increased from 300 to 1,200 rpm to maintain the level of dissolved oxygen above 20%. Working volume was 3 L.

After 90 hours fermentation, the amount of erythritol from 30% glucose is measured by HPLC equipped with Carbohydrate Analysis column. The obtained erythritol is 160 g/L, volumetric productivity is 1.78 g/L.h.

EXAMPLE XI

The frozen (−70° C.) mutant cells of Pichia sp. (KCCM-10129) are cultivated in a 250-ml flask containing 50 ml growth medium(0.8~1.2% glucose, 0.4~0.6% peptone, 0.3~0.5% yeast extract and 0.2~0.4% malt extract) at 28~32° C. and 220~260 rpm. The seed cells are cultivated in a 5 L fermentor for producing erythritol in main culture. Fermentor experiments with fermentation medium were performed at 30° C. and pH 5.5 during the fermentation. Aeration rate was in the range of 0.5~2.0 vvm. Agitation speed was gradually increased from 300 to 1,200 rpm to maintain the level of dissolved oxygen above 20%. Fed-batch culture was performed with initial medium of 1.8 L and finial volume was 3 L by adding continuously 1.2 L of feeding medium. The initial medium of 1.8 L, consisted of 180 g glucose and 60 g yeast extract, 15 g $KH_2PO_4$ and 0.6 g $MgSO_4.7H_2O$. The feeding medium of 1.2 L contained 1020 g glucose and 60 g NaCl was added at 20 hours. The concentration of glucose during fermentation could be controlled in the range of 11.0~13.0% by adjusting pump speed of the feeding medium.

After 72 hours fermentation, the amount of erythritol from 40% glucose is measured by HPLC equipped with Carbohydrate Analysis column. The obtained erythritol is 212 g/L, volumetric productivity is 2.94 g/L.h.

We claim:
1. The novel mutant cells of Pichia sp. (KCCM-10129).

* * * * *